(12) United States Patent
Palero et al.

(10) Patent No.: US 10,448,997 B2
(45) Date of Patent: Oct. 22, 2019

(54) MEASUREMENT DEVICE FOR SKIN PROPERTIES AND NON-INVASIVE TREATMENT DEVICE

(71) Applicant: KONINKLIJKE PHILIPS N.V., Eindhoven (NL)

(72) Inventors: Jonathan Alambra Palero, Eindhoven (NL); Martin Jurna, Eindhoven (NL); Babu Varghese, Eindhoven (NL); Margaret Ruth Horton, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 8 days.

(21) Appl. No.: 14/896,760

(22) PCT Filed: Jun. 25, 2014

(86) PCT No.: PCT/EP2014/063323
§ 371 (c)(1),
(2) Date: Dec. 8, 2015

(87) PCT Pub. No.: WO2014/207003
PCT Pub. Date: Dec. 31, 2014

(65) Prior Publication Data
US 2016/0120604 A1    May 5, 2016

(30) Foreign Application Priority Data

Jun. 25, 2013  (EP) ..................................... 13173476

(51) Int. Cl.
*A61B 18/20*  (2006.01)
*A61N 5/06*   (2006.01)
(Continued)

(52) U.S. Cl.
CPC .......... *A61B 18/203* (2013.01); *A61B 5/0059* (2013.01); *A61B 5/441* (2013.01);
(Continued)

(58) Field of Classification Search
CPC ............................. A61B 5/0084; A61B 5/0059
See application file for complete search history.

(56) References Cited

U.S. PATENT DOCUMENTS

| 5,207,670 A | 5/1993 | Sinofsky |
| 5,409,481 A | 4/1995 | Poppas |

(Continued)

FOREIGN PATENT DOCUMENTS

| JP | 04132540 A | 5/1992 |
| WO | 2011080574 A1 | 7/2011 |

OTHER PUBLICATIONS

Tian, L., H. Wei, et al. (2011), "Backward Emission Angle of Microscopic Second-Harmonic Generation From Crystallized Type I Collagen Fiber", Journal of Biomedical Optics 16(7): 075001-075-001.

*Primary Examiner* — Hien N Nguyen

(57) ABSTRACT

The application provides a non-invasive measurement device (30) and method for the measurement of skin properties using laser light, the device comprising a probe module (70) and an imaging module (50). The application also provides a non-invasive treatment device (130, 230, 330, 430) and method comprising the measurement device/method. The probe module (70) provides a probe light beam (82) that enters the skin along the probe axis (71). The probe light beam (82) is separate from any treatment radiation beam (22), so that the probe light beam (82) can be optimized for the measurement. A more reliable skin measurement system is provided because it measures a plurality of positions along the probe axis (71), within a probe region (95). The measurement device and method may also com-
(Continued)

prise a treatment module (110) or treatment step. The skin parameters measured may then be directly used to control the treatment parameters. This results in a skin treatment device (10) being provided that is both effective and delivers reproducible results.

10 Claims, 6 Drawing Sheets

(51) Int. Cl.
    *A61B 5/00*     (2006.01)
    *A61B 18/00*     (2006.01)

(52) U.S. Cl.
    CPC .... *A61N 5/0616* (2013.01); *A61B 2018/0047* (2013.01); *A61B 2018/00458* (2013.01); *A61B 2018/00785* (2013.01); *A61N 2005/0628* (2013.01)

(56) References Cited

U.S. PATENT DOCUMENTS

| | | |
|---|---|---|
| 6,015,404 A | 1/2000 | Altshuler |
| 6,190,377 B1 | 2/2001 | Kuzdrall |
| 6,413,267 B1 | 7/2002 | Dumoulin-White |
| 6,659,999 B1 | 12/2003 | Anderson |
| 7,824,395 B2 | 11/2010 | Chan |
| 2005/0154382 A1 | 7/2005 | Altshuler |
| 2005/0254381 A1 | 11/2005 | Desormeaux, Jr. |
| 2007/0252997 A1 | 11/2007 | Vanhal |
| 2007/0260230 A1 | 11/2007 | Youngquist |
| 2007/0278140 A1* | 12/2007 | Mallett ............... B07C 7/005 705/308 |
| 2008/0215038 A1 | 9/2008 | Bakker |
| 2008/0215040 A1 | 9/2008 | Paithankar |
| 2010/0114080 A1 | 5/2010 | Theriault |
| 2010/0130969 A1 | 5/2010 | Batterson |
| 2012/0283712 A1 | 11/2012 | Youngquist |
| 2013/0060104 A1* | 3/2013 | Schlottau ........... A61B 5/14558 600/310 |

\* cited by examiner

MEASUREMENT DEVICE FOR SKIN PROPERTIES AND NON-INVASIVE TREATMENT DEVICE

This application is the U.S. National Phase application under 35 U.S.C. § 371 of International Application No. PCT/EP2014/063323, filed on Jun. 25, 2014, which claims the benefit of International Application No. 13173476.6 filed on Jun. 25, 2013. These applications are hereby incorporated by reference herein.

FIELD OF THE INVENTION

The invention relates generally to the measurement of skin properties, in particular properties relevant for the treatment of skin using electromagnetic treatment radiation, such as laser light. It relates even more particularly to a non-invasive device and method for skin treatment in which these measurements are made and used to modify or control the skin treatment.

BACKGROUND OF THE INVENTION

Various forms of electromagnetic radiation, particularly laser light beams, have been used on skin for many years for a variety of treatments, such as hair removal, skin rejuvenation to reduce wrinkles, and the treatment of conditions such as acne, actinic keratoses, blemishes, scar tissue, discoloration, vascular lesions, acne treatment, cellulite and tattoo removal. It is well-known that some of these treatments may be performed to provide a therapeutic effect, but frequently they are all performed to provide a non-therapeutic or cosmetic effect. Most of these treatments rely on photothermolysis, where a treatment location is targeted by the treatment radiation. For example, to treat wrinkles, the dermis layer is damaged by heating (thermolysis) to induce a wound response without damage to the epidermis.

In some treatments, said heating by electromagnetic radiation takes place in the dermal layer by using radiation which can penetrate the skin as far as the dermal layer. FIG. 1 schematically shows a skin treatment device 10 known in the art, comprising a radiation source 20, and beam shaping and directing components 27. The radiation source 20 provides an incident radiation beam 22 suitable for treating human or animal skin. The radiation used may be any type of electromagnetic or thermal radiation which provides a beneficial effect in the skin. For example, when using laser light, the skin treatment device 10 may comprise a pulsed laser light source 20 such as a Nd:YAG laser with emission at 1064 nm and 1-1000 µs pulse duration.

The beam shaping and directing components 27 receive the radiation beam 22 from the radiation source 20, and create a radiation beam 22 with the desired properties which exits the device 10 along a treatment axis 21.

For example, when using laser light, these beam shaping and directing components 27 may be optical elements, such as mirrors, lenses, beam splitters, prisms etc, for directing the laser light beam 22 to exit the device along a treatment axis 21, and for focusing the light beam 22 inside the skin at a treatment location 90 on the treatment axis 21.

In a further example, if radio-frequency radiation is used, these beam shaping and directing components 27 may be waveguides, apertures, reflectors etc. for directing the radio-frequency beam 22 to exit the device along a treatment axis 21.

The skin comprises multiple layers with different radiation transmission and absorption properties. The epidermis 16 is composed of the outermost layers and forms a waterproof protective barrier. The outermost layer of the epidermis is the stratum corneum which, due to its microscopic fluctuations in roughness, impedes the coupling of radiation, in particular light, between the device 10 and the skin. Typically, a radiation coupler 12 is used between the device 10 where the radiation beam exits and the skin surface where the radiation enters into the skin. This optimizes the penetration of the treatment radiation beam 22 into the skin. For example, in the case of a laser light beam 22, an optical coupler 12 may be used which comprises lenses, mirrors, prisms, an index-matching fluid or a combination thereof. Underneath the epidermis 16, the dermis 17 is situated which is the region at which many of the skin treatments are directed.

If the device 10 is used to reduce wrinkles in the skin, the treatment location 90 is in the collagen of the dermis 17 in order to create microscopic lesions at the treatment location, which results in new collagen formation.

The laser light treatment devices 10 use the fact that the skin transmits electromagnetic radiation that is to be focused to a very small focal spot in the dermis 17. To maximize this effect, the wavelength of the laser light is between 800 and 1100 nm. In this range, transmission is high and scattering and linear absorption are low. Thus, phenomena exploited using a skin treatment, such as photothermolysis or laser induced optical breakdown (LIOB), may be achieved easily, accurately (i.e. very locally) and efficiently. It is however not excluded to use other wavelengths.

An increasing number of these non-invasive skin treatment devices are being provided for use by consumers instead of by medical professionals. Such uses are mainly for cosmetic or non-therapeutic reasons. Such home use raises new concerns, such as safety and treatment efficacy. This is particularly important when the radiation source 20 is high-powered, for example a laser.

For successful and safe skin treatments, it is crucial that the appropriate amount of energy be delivered to the treatment location 90. Delivery of too much energy results in undesirable side effects, such as scarring or burning of the skin. Delivery of too little energy results in low-efficacy treatment. Also, even under normal circumstances, reproducibility of the treatment results may vary between persons and even between anatomical regions on the same person. This is due to the inherent variability of skin properties that critically affect energy delivery efficiency.

There is thus a need for radiation skin treatment devices that are both effective and deliver reproducible results.

SUMMARY OF THE INVENTION

An object of the invention is to provide a non-invasive measurement device and a method of measuring skin properties which are relevant for skin treatments.

The object is achieved according to the invention by means of a non-invasive measurement device for the measurement of skin properties using laser light, the device comprising a probe module and an imaging module, wherein:

the probe module comprises a first optical system and a laser light source for generating a probe light beam, the probe module being configured and arranged such that, in use, the probe light beam exits the device along a probe axis and impinges on an outer surface of the skin to be treated;

the first optical system being configured and arranged to direct, in use, the probe light beam to a probe region inside the skin;

the imaging module comprises a second optical system and an optical detector array, the optical detector array being disposed along a detector axis comprised in an image plane of the second optical system, the second optical system being configured and arranged to form, in use, an image on a plurality of light detection elements comprised in the optical detector array of, respectively, a plurality of probe positions distributed along the probe axis within the probe region, wherein the second optical system has an imaging optical axis that intersects with the probe axis.

The object of the invention is also achieved by providing a method for non-invasive measurement of skin properties using a device generating laser light, the device comprising a probe module and an imaging module, the method comprising:

providing a probe module comprising a first optical system and a laser light source for generating a probe light beam;

configuring and arranging the probe module such that, in use, the probe light beam exits the device along a probe axis and impinges on an outer surface of the skin to be treated;

configuring and arranging the first optical system to direct, in use, the probe light beam to a probe region inside the skin;

providing an imaging module comprising a second optical system and an optical detector array, the optical detector array being disposed along a detector axis comprised in an image plane of the second optical system;

configuring and arranging the second optical system to form, in use, an image on a plurality of light detection elements comprised in the optical detector array of, respectively, a plurality of probe positions distributed along the probe axis within the probe region, wherein the second optical system has an imaging optical axis that intersects with the probe axis.

The invention is based on the insight that skin measurement devices known in the art are inherently limited because they only measure specific parameters of the skin at the treatment location during the application of the treatment radiation. The invention provides a probe light beam that enters the skin along the probe axis. The probe light beam is a radiation beam separate from the treatment radiation beam (which may be used before, during or after the measurement), so that the characteristics of the probe light beam may be predetermined before the measurement. The probe module may therefore be optimized for the measurement.

A second insight is that, although the properties of the treatment location are important, the treatment radiation beam passes through the skin between the outer layer of the skin and the treatment location and the energy directed to the treatment location will spread to surrounding tissue. Consequently, the invention provides a more reliable skin measurement system, because it measures a plurality of positions along the probe axis, within a probe region. As the treatment location is (or will be after the measurement) comprised within this probe region, the invention measures the skin properties at the treatment location and the surrounding points along the probe axis. Known measurement devices, such as described in US 2005/0154382, US 2007/0252997, and US 2010/0130969 do not image a plurality of points along the probe axis.

A third insight is that a more reliable measurement is provided when the plurality of positions are imaged by an imaging module. Many measurement devices known in the art, such as the device described in US 2008/0215038, simply make an image of the top surface of the skin and try to interpret the skin properties from this image. Because the invention comprises an imaging module and a probe module, the angle between the probe axis and the imaging optical axis is predetermined, and the angle between the probe axis and the outer layer of the skin is also predetermined. The second optical system may thus be configured and arranged such that the plurality of points lie in an object plane of the second optical system, and such that the optical detector array is disposed in the image plane of the second optical system. This means that a plurality of points are imaged at the same time using, respectively, a plurality of light detection elements comprised in the detector array.

In other words, the measurement device provides an optical depth profile of the section of probe axis comprising the plurality of points—these are the positions in the skin that are relevant for the treatment—by measuring either during treatment, or before treatment, or after treatment. The skin parameters measured may then be used to set or modify the treatment parameters, or to indicate that no further treatment is required.

So, this measurement device and method are fast, accurate and can provide appropriate skin physiological information which is relevant for the optimisation of the radiation treatment.

It may be advantageous to further configure the measurement device such that the detector axis is comprised in a plane which comprises the probe axis and the imaging optical axis. This may result in fewer aberrations in the image on the optical detector array, reducing the need to correct the image to compensate for the detector axis not being in the same plane.

It may also be advantageous to configure and arrange the measurement device such that an angle enclosed by the probe axis and the imaging optical axis is in a range of 20 to 90 degrees. The use of an imaging module means that there is considerable flexibility in the position of each component within the measurement device, allowing the device dimensions to be minimized or to be defined to make operation simpler. This is particularly advantageous when the measurement device is used by a consumer.

It may also be advantageous to configure and arrange the measurement device such that, during operation of the measurement device, an angle enclosed by the probe axis and the skin outer surface is in a range of 45 to 90 degrees. To be able to measure at the plurality of points, the probe light beam must penetrate the skin to the desired positions of the treatment location, so that an angle greater than 45 degrees is preferred. The image of the plurality of probe positions may be affected by the distance and tissue type between each probe position and the outer surface of the skin. Therefore, it is preferable to dispose the imaging optical axis such that the distance between the outer surface of the skin and each of the probe positions is as similar as possible.

It may be even more advantageous to configure and arrange the measurement device such that the detector axis and the probe axis are parallel to each other. This may be achieved by predefining the lens planes of the second optical system so as to be parallel to the probe axis. Although the optical detector array may be tilted from this parallel position to compensate for any deviation from parallel of the lens planes, the parallel detector axis configuration is expected to provide the simplest and fastest measurement system.

It may be advantageous for the measurement method to further comprise:

processing the image detected by the optical detector array to generate one or more control parameters;

applying the one or more control parameters to determine operating parameters of the probe laser light source and/or the first optical system.

This makes it possible for the skin properties measured by the device to be immediately used to improve or modify the measurement. For example, if the average intensity is too low, the operating parameters of the probe laser light source may be adapted to provide more energy.

The object of the invention is also achieved by providing a non-invasive treatment device for treatment of skin using electromagnetic treatment radiation, the device comprising a measurement device according to the invention, and the treatment device further comprising a treatment module, wherein:

the treatment module comprises a treatment radiation source for providing a treatment radiation beam and beam-shaping and directing components, the treatment module being configured and arranged such that, in use, the treatment radiation beam exits the device along a treatment axis and impinges on an outer surface of the skin to be treated; the beam-shaping and directing components being configured and arranged to direct, in use, the radiation treatment beam to a treatment location disposed within the probe region.

The object of the invention is also achieved by a method of non-invasive skin treatment using electromagnetic treatment radiation comprising a measurement method according to the invention, the method of treatment further comprising:

providing a treatment module comprising a treatment radiation source for providing a treatment radiation beam and beam-shaping and directing components;

configuring and arranging the treatment module such that, in use, the treatment radiation beam exits the device along a treatment axis and impinges on an outer surface of the skin to be treated;

configuring and arranging the beam-shaping and directing components to direct, in use, the treatment radiation beam to a treatment location disposed within the probe region.

By including the treatment module into the measurement device, a treatment device is provided. The angle between the probe axis and the treatment axis may be predetermined, thus enabling the treatment location to be at a desired position within the probe region. This increases the reproducibility of the measurement, because the differences in position between the probe region and the treatment location are limited.

It may be advantageous for a treatment method according to the invention to further comprise:

processing the image detected by the optical detector array intensity to generate one or more control parameters;

applying the one or more control parameters to determine operating parameters of the treatment radiation source and/ or the beam-shaping and directing components.

By virtue thereof, the skin properties measured by the device can be immediately used to improve or modify the treatment. For example, if the skin properties indicate that the presence of collagen is not detected, the position of the treatment location may be changed.

If the treatment radiation is laser light, it may be particularly advantageous to configure and arrange a treatment module as described, in such a manner that the treatment axis coincides with the probe axis. This further improves reproducibility because the treatment location is more likely to be disposed in the probe region.

It should be noted that items which have the same reference numbers in different Figures, have the same structural features and the same functions, or are the same signals. When the function and/or structure of such an item have been explained, there is no necessity for repeated explanation thereof in the detailed description.

DETAILED DESCRIPTION OF EXAMPLES

Figure 2:
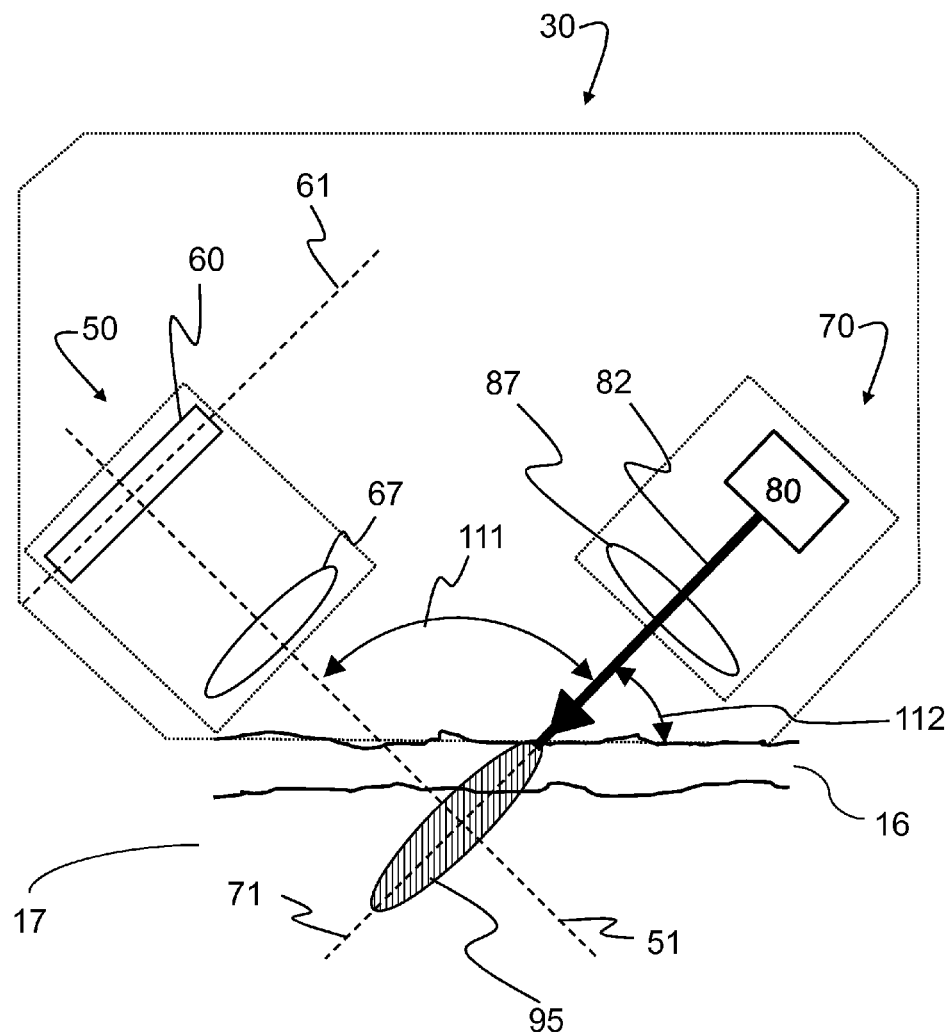
FIG. 2 shows a first embodiment 30 of a non-invasive measurement device for measuring skin properties using laser light, which comprises a probe module 70 and an imaging module 50.

FIG. 2 illustrates a first embodiment 30 of the invention. It depicts a non-invasive measurement device 30 for the measurement of skin properties using laser light. The measurement device comprises a probe module 70 and an imaging module 50 with a fixed relative disposition.

The probe module comprises a laser light source 80 and a first optical system 87 to receive the laser light from the source 80, and to direct the laser light beam 82 to an aperture in the measurement device 30. The probe module 70 is configured and arranged such that, in use, the probe light beam 82 exits the device 30 along a probe axis 71 and impinges on an outer surface of the skin to be treated. The first optical system 87 is configured and arranged to direct, in use, the probe light beam 82 to a probe region 95 inside the skin.

The probe laser light source 80 is selected to provide laser light which penetrates the skin to a sufficient depth, with the appropriate properties depending on the anticipated physiological changes expected in the probe region 95 of the skin during radiation treatment, and the method is selected to measure a related skin property.

The device 30 may also comprise an optical coupler 12 to optimize the energy delivery to the treatment location 90. Any suitable optical coupler 12, such as those known in the art, may be used.

The imaging module 50 comprises a second optical system 67 and an optical detector array 60, the optical detector array 60 being disposed along a detector axis 61 comprised in the image plane of the second optical system 67. The second optical system 67 is configured and arranged such that, in use, an image on a plurality of optical detectors comprised in the optical detector array 60 of, respectively, a plurality of probe positions distributed along the probe axis 71 within the probe region 95 is obtained. The imaging optical axis 51 of the optical system 67 intersects with the probe axis 71 within the probe region 95 due to the fixed relative disposition of the probe 70 and imaging module 50 within the device 30.

Figure 3:
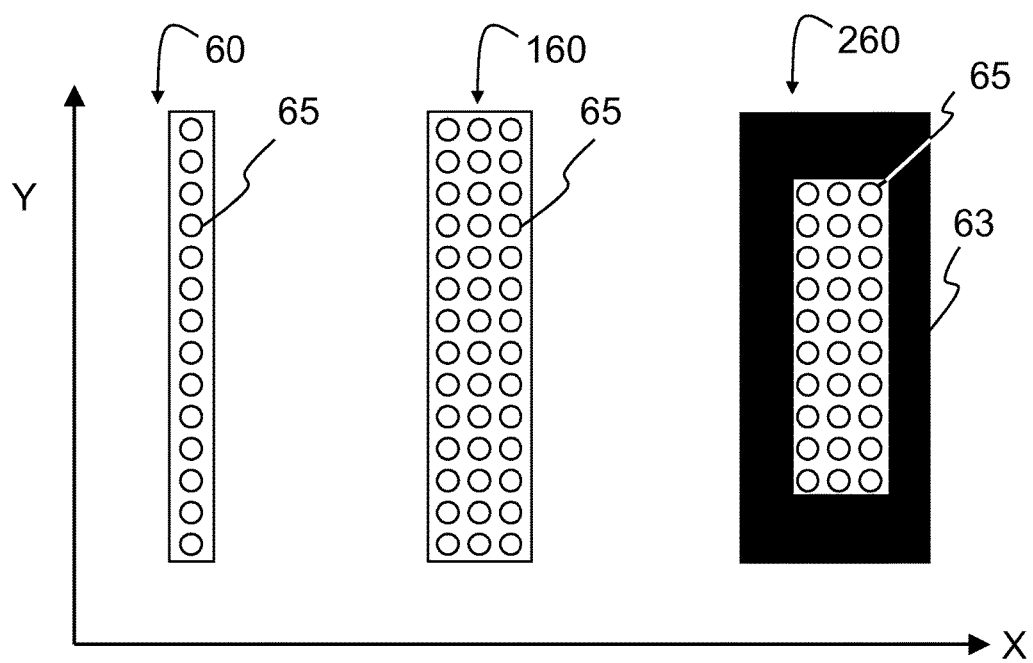
FIG. 3 depicts three examples of a suitable optical detector array 60, 160, 260.

The optical detector array 60, 160, 260 may be a linear array of individual light sensors 65, as depicted in FIG. 3—in other words, a plurality of light sensors disposed at equal distances from each other along a longitudinal axis. Typically, the light collected by the optical detector array 60, 160, 260 is converted into an electrical signal via a circuit that may be built into the array substrate. Each of the plurality of probe positions is imaged onto the detector array onto one or more of the optical detectors.

As the imaging module 50 images a plurality of probe positions along the probe axis 71, the detector array 60 needs to be rectangular—that is, the longitudinal axis of the array 60 is disposed along the detector axis 61. In other words, if the detector, during use, comprises a matrix of Y light detection elements 65 in the direction extending along the detector axis 61 times X light detection elements 65 in the direction extending along a further axis perpendicular to the detector axis 61, then Y will be larger than X. Y is the direction of the longitudinal axis of the detector array 60.

In the first example 60 depicted in FIG. 3, X is 1 and Y is 14. This makes it suitable for measuring 14 probe positions along the probe axis 71. This may be, for example, a linear CCD detector.

In the second example 160 of FIG. 3, X is 3 and Y is 14. This also makes it suitable for measuring 14 probe positions along the probe axis 71. In that case, either only signals from the centre column (extending in Y direction) of the detector array 160 are considered, or the signals from each row (extending in X direction) are combined in some way, such as averaging. Similarly, light sensors 65 in Y direction may also be combined in some ways, for example, to measure 7 probe positions along the probe axis 71. If multiple light sensors 65 in Y direction are used, substantially increased spatial information on the treatment profile can be obtained, e.g. lesion width, and greater flexibility in laser treatment efficacy improvement is achieved.

In the third example 260 of FIG. 3, a linear array is formed using a large number of light sensors 65 extending in both X and Y directions, such as a CCD array, but light sensors that are not required are covered with a mask 63. Alternatively, the electrical signals from light sensors 65 that are not required may simply be ignored when the signals are processed, or these signals may not be used.

A Y to X ratio of light detection elements is preferably greater than or equal to 5 to 1.

Multiple detectors are known in the art, such as in published U.S. Pat. No. 6,413,257. This patent discloses the use of a plurality of detectors to monitor the energy characteristics of skin tissue during treatment. Two to four infrared detectors are disposed such that they measure the radial dependence of the diffuse radiation emitted from the treatment location. The treatment radiation enters the skin at 90 degrees, and the detectors are disposed at different distances from the entry point into the skin. However, the detectors disclosed are simply infrared intensity detectors—no image is formed of the treatment location.

The imaging module 50 may then be further configured to detect the desired optical signal from the skin, by additionally providing it with optical components such as wavelength filters and/or by appropriate processing 40 of the signals from the optical detector array 60. The configuration required depends upon the type of treatment that the measured skin properties are to be used for, and the position of the treatment location 90 in the skin.

Example 1 the optical signal is a Second-Harmonic Generation (SHG) signal, which may indicate the presence of collagen. The probe laser light source 80 may then be pulsed (femtosecond to nanosecond range) at a wavelength in the range of 700 to 2200 nm. The optical signal measured will depend on the related skin properties, namely the collagen denaturation state, the dermal 17 depth and the epidermal 16 thickness.

Example 2 the optical signal is 1-photon and 2-photon excited autofluorescence, which may indicate the presence of stratum corneum (namely keratin and lipids), epidermal cells, NAD (P)H, collagen, elastin, hair. The probe laser light source 80 for 1-photon excitation may be a continuous wave laser light source operating at a wavelength in the range of 300 to 500 nm, or for 2-photon excitation it may be pulsed (femtosecond to nanosecond range) operating at a wavelength in the range of 600 to 1000 nm. The optical signal measured will depend on the related skin properties, namely strateum corneum thickness, epidermal 16 thickness, dermal 17 depth, hair thickness, hair depth, melanin concentration, basal layer depth and melanocyte depth.

Example 3 the optical signal is Rayleigh-scattering, which may indicate the presence of scattering centers. The probe laser light source 80 may then be a continuous wave or pulsed laser light source operating at a wavelength in the range of 350 to 1100 nm. The optical signal measured will depend on the related skin properties, namely melanocyte depth, basal layer depth, epidermal thickness 16, and tissue coagulation state.

Example 4 the optical signal is Raman-scattering, which may indicate the presence of lipids, water or collagen. The probe laser light source 80 may then be a continuous wave or pulsed nanosecond range laser light source operating at a wavelength in the range of 350 to 1100 nm. The optical signal measured will depend on the related skin properties, namely strateum corneum thickness, water concentration and collagen denaturation state.

Example 5 the optical signal is a second- or third-harmonic generation signal, which may indicate the presence of tissue interfaces or membranes. The probe laser light source 80 may then be pulsed (femtosecond to nanosecond range) at a wavelength in the range of 1050-3300 nm. The optical signal measured will depend on the related skin properties, namely strateum corneum thickness, epidermal 16 thickness, and dermal 17 depth.

Example 6 the optical signal is infrared thermal radiation, which may indicate the presence of heated tissue. The probe laser light source 80 may then be a continuous wave or pulsed laser light source operating at a wavelength in the range of 350 to 1100 nm. The optical signal measured will depend on the related skin properties, namely temperature.

The skilled person will be able to configure the measurement device 30 to perform the measurement required. This may be done using simulation calculations, or based upon trial and error.

The skilled person will also realise that the measurement device may comprise a plurality of probe 70 and imaging 50 modules, each one configured to perform the measurement of one or more optical properties. Each module may also be configured to perform different measurements by using a laser source 80 operating at a variable wavelength and/or an optical detector array 60 sensitive to selectable wavelengths.

In FIG. 2, the device is configured such that the probe axis 71 makes an angle 112 of about 45 degrees with the axis coinciding with the outer layer of skin 11. The device is further configured such that the imaging optical axis 51 makes an angle 111 of about 90 degrees with the probe axis 71. This configuration may result in a reduced amount of aberration in the measurement because the distances between the outer skin surface and the probe positions are of a similar order of magnitude. Additionally, the angle of about 90 degrees between the probe axis 71 and the imaging optical axis 51 means that the lens planes of the second optical system 67 are approximately parallel to the probe axis 71—in other words, the plurality of probe positions along the probe axis 71 are located in the object plane and the optical detector array is located in the image plane of the second optical system 67.

Figure 5A:
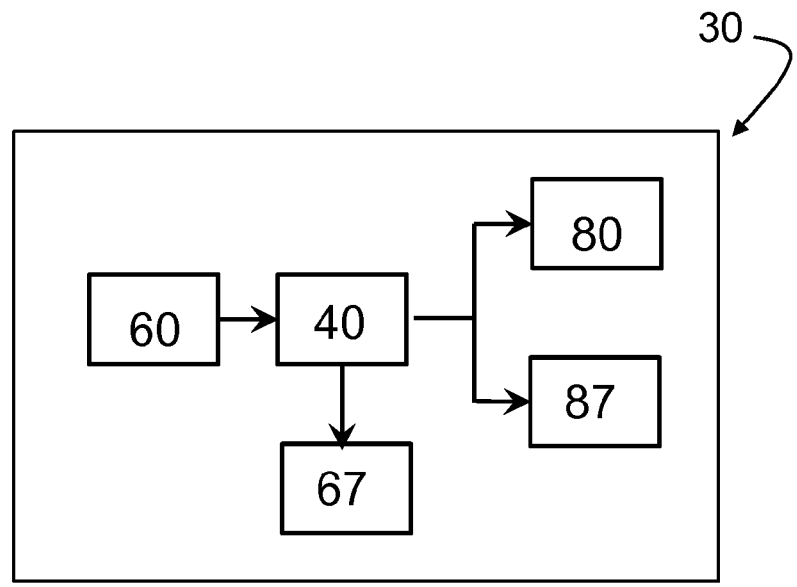
FIGS. 5A and 5B schematically show possible control connections between the different components of the first embodiment 30 and the second embodiment 130, respectively, and FIGS. 6A to 6D schematically illustrate the relative angles between the probe axis 71, the imaging optical axis 51 and the outer surface of the skin axis 11 for, respectively, the first 30 and second 130 embodiment, the third embodiment 230, the fourth embodiment 330 and the fifth embodiment 430.

The measurement device may further comprise a processor 40 for processing the signals from the optical detector array 60 to determine the required skin properties. As depicted in FIG. 5A, the processor 40 may also be electrically connected to adjustable components of the second optical system 67 to optimise imaging.

The processor 40 may also be electrically connected to the probe laser light source 80 and/or adjustable components of the first optical system 87. This may be used to optimize the probe module 70 by adjusting, for example, the probe laser intensity, pulse rate, focus, and the position of the probe axis 71.

The skin properties measured by the invention may be used to determine the parameters for a subsequent treatment using electromagnetic radiation, or to indicate that a treatment currently in progress should be modified or even stopped, or to indicate that no further treatment is required. The measurement device may further comprise an indication system to make these results known to the user, such as a green and red led or an audible warning.

In another example, the measurement device and method may be used to characterize the skin within a zone of the body. These measurements may be converted into a map of specific positions, or combined in some way, such as averaging, to determine a single set of skin properties for the whole zone. The outcome may then be made known to the user, or provided in some way to the subsequent treatment device.

After treatment, the characterization may be repeated to monitor the progress of the treatment, and to prevent excess treatment.

The invention may also be used to create look-up tables for multiple body zones and a multiplicity of individuals, so that typical treatment settings may be provided for different treatment devices.

For some treatments it may be possible to measure the skin properties before, during or after the treatment, or some combination thereof.

Figure 4:
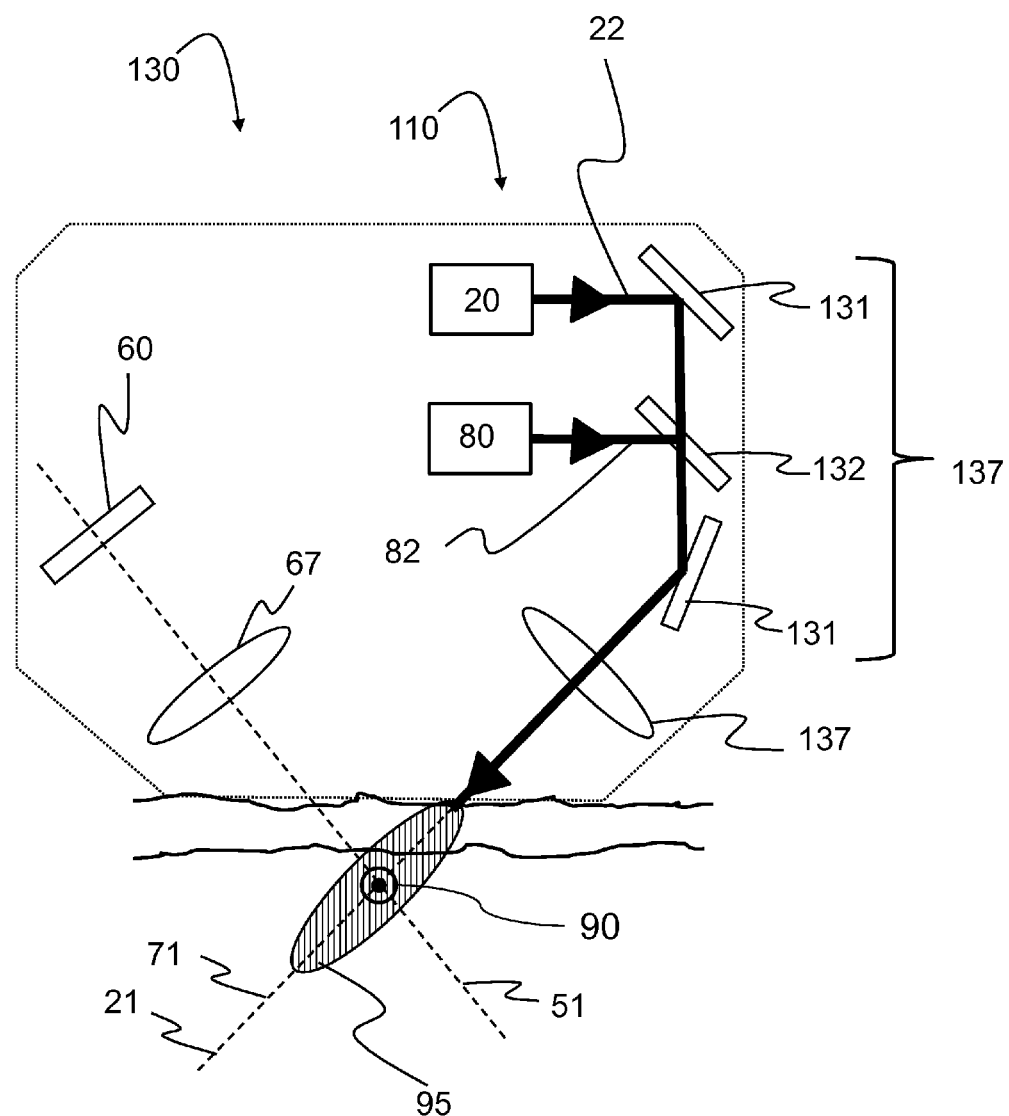
FIG. 4 depicts a second embodiment 130 of a non-invasive measurement device for measuring skin properties using laser light, which comprises a probe module 70, an imaging module 50 and a treatment module 110.

As depicted in FIG. 4, a treatment module 110 may also be comprised in the measurement device of FIGS. 2 and 3. This may also be described as a treatment device 130 comprising a measurement device 30. The probe module 70 and imaging module 50 are the same as described in relation to FIGS. 2 and 3.

Figure 1:
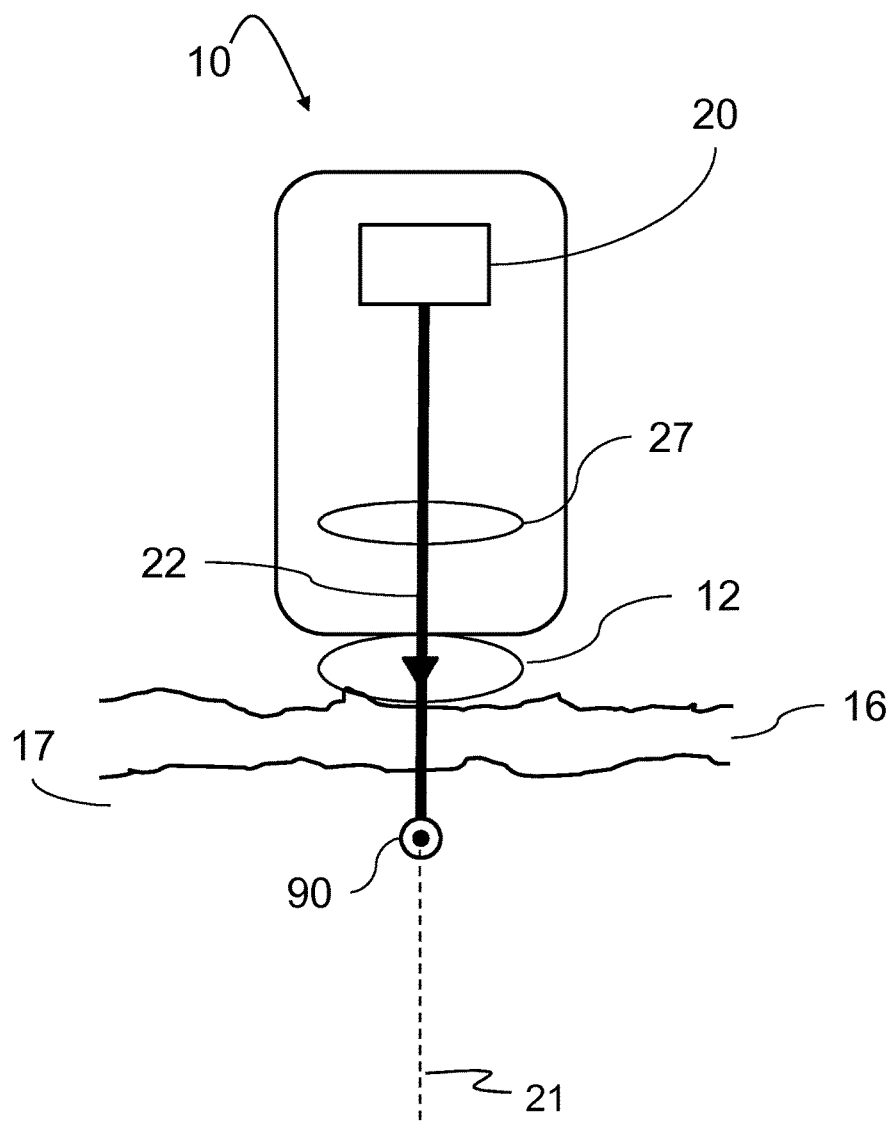
FIG. 1 diagrammatically shows a non-invasive radiation treatment device in the process of treating skin, which is known in the art.

The functionality of the treatment module 110 is similar to the functionality of the treatment device 10 depicted in FIG. 1.

In FIG. 4, the treatment module 110 comprises a treatment radiation source 20 for providing a treatment radiation beam 22 and beam-shaping and directing components 137, the treatment module 110 being configured and arranged such that, in use, the treatment radiation beam 22 exits the device through an aperture 130 along a treatment axis 21 and impinges on an outer surface of the skin to be treated; the beam-shaping and directing components 137 being configured and arranged to direct, in use, the radiation treatment beam 22 to a treatment location 90 disposed within the probe region 95.

When using, for example a radio-frequency based treatment, it may be difficult to keep the treatment location 90 within the probe region 95. To improve the resolution of the probe points along the probe axis 71, it may be advantageous for the imaging module 50 to further comprise a confocal slit disposed at the conjugate plane of the second optical system 67 to minimize out-of-focus signals.

The treatment axis 21 may be arranged to be disposed proximate and parallel to the probe axis 71. This may be advantageous if the treatment module 110 is configured to cause tissue ablation, and the separation of the probe axis 71 and the treatment axis 21 is arranged such that the probe positions to be imaged are not ablated, but only heated by the treatment radiation.

FIG. 4 further depicts the second embodiment 130 of a non-invasive measurement device for measurement of skin properties using laser light, which comprises a laser beam probe module 70, an imaging module 50 and a laser beam treatment module 110. The treatment module 110 comprises a treatment laser radiation source 20 for providing a treatment light beam 22 and a third optical system 137, the treatment module 110 being configured and arranged such that, in use, the treatment light beam 22 exits the device 130 through an aperture along a treatment axis 21 and impinges on an outer surface of the skin to be treated, and optical system 137 being configured and arranged to direct, in use, the light treatment beam 22 to a treatment location 90 disposed within the probe region 95.

The optical elements 131, 132 found in the optical system 137 may comprise one or more lenses for converging and/or diverging the light beam 21, and one or more mirrors 131 for deflecting the light beam in a desired direction. The exact position and/or orientation of the optical elements may be adjustable using techniques known in the art to adapt the position and quality of the light beam 22 such that the beam is focused at the treatment location 90. Focus control may be provided by adjusting the position of one or more of the lenses and/or rotating one or more of the mirrors.

The number and positions of lenses and mirrors 131 are determined by the disposition of the components within the third optical system 137 and the desired degrees of adjustment that the skilled person wishes to provide.

For example, the treatment laser source 20 may be a pulsed Nd:YAG laser at 1064 nm with sufficient pulse energy in the laser treatment beam 22 to heat the treatment location 90 and cause thermal damage, e.g. photocoagulation.

The probe laser beam 82 may be configured to have sufficient peak intensity to induce SHG in collagen in the dermis 17. It is known from Tian, L., H. Wei, et al. (2011), "Backward emission angle of microscopic second-harmonic generation from crystallized type I collagen fiber.", Journal of Biomedical Optics 16 (7): 075001-075001 that the SHG radiation pattern in collagen Type I is characterized by both forward and backward propagated light, as well as non-axial side lobes. It is estimated that this, together with the anisotropic nature of skin tissues, may allow a significant amount of SHG signals to propagate through the tissue in a direction perpendicular to the treatment axis 21.

The imaging module's optical system 67 and the optical detector array may be configured to have a maximum spectral transmission and efficiency, respectively, for optimum sensitivity to the SHG signal. Typically, this is achieved by using an appropriate spectral filter, such as one having a narrow bandwidth centered around the half wavelength of the probe laser source 80. In this example, the wavelength of the SHG signal is 532 nm for a 1064 nm laser source. The information that is obtained from the SHG depth profile includes depth of dermis 17, epidermal 16 thickness, and collagen denaturation state.

The treatment module 110 may be configured and arranged to provide the treatment axis 21 along the probe axis 71. Such an arrangement may be advantageous because the probe positions being imaged coincide with the region being treated and such an arrangement is expected to give more accurate measurement results to optimize the treatment.

If the treatment radiation beam 22 is laser light, the third optical system 137 may be configured and arranged to direct both the treatment laser beam 22 and the probe light beam 82, as depicted in FIG. 4. However, the skilled person will realize that the functions performed by the probe module 70 and the treatment module 110 may be implemented in completely separate hardware, the only requirement being that the treatment 110 and probe 70 modules have a fixed relative disposition—in other words, the relationship between the treatment axis 21, the probe axis 71, the treatment location 90 and the probe region 95 must be known, so that the measurements being made can be related to the skin treatment. The way in which the treatment 110 and probe 70 modules are implemented depends mainly on the type of radiation used for the treatment beam 21.

Figure 5B:
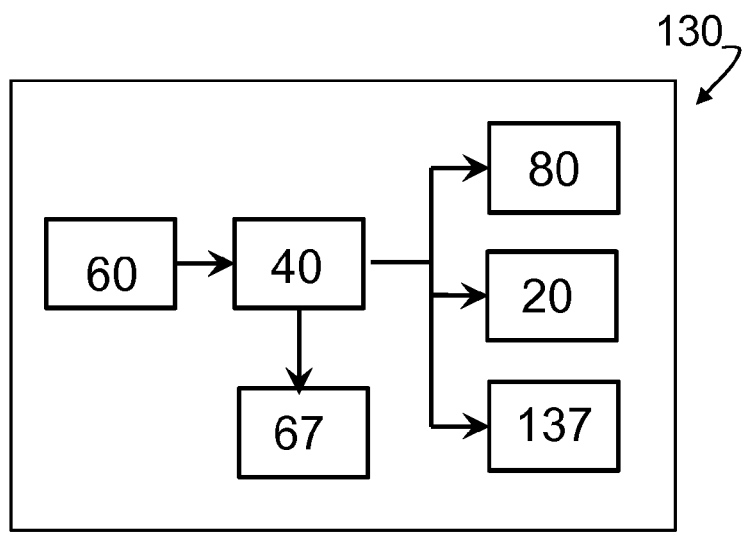

The treatment device 130 may further comprise a processor 40 for processing the signals from the optical detector array 60 to determine the required skin properties. As depicted in FIG. 5B, the processor 40 may also be electrically connected to adjustable components of the second optical system 67 to optimize imaging.

The processor 40 may also be electrically connected to the probe laser light source 80 and/or adjustable components of the first optical system 87. This may be used to optimize the probe module 70 by adjusting, for example, the probe laser intensity, pulse rate, focus, and the position of the probe axis 71.

The processor 40 may also be electrically connected to the treatment radiation source 80 and/or adjustable components of the third optical system 87. This may be used to optimize the treatment module 110 by adjusting, for example, the treatment radiation fluence, the pulse duration, pulse rate, the focus, and the position of the treatment location 90.

The treatment parameters implemented in the treatment module 110 may be based on the desired nature and level of treatment and on the measurement of skin properties by means of the invention. The skin properties that may be used include:

(1) skin component layer depth (dermis layer depth, melanocyte layer depth, basal cell layer depth);

(2) skin component thickness (stratum corneum thickness, epidermal thickness, hair thickness);

(3) skin component concentration depth profile (melanin concentration profile, water concentration profile);

(4) skin component denaturation depth profile (collagen denaturation state);

(5) tissue coagulation depth profile, and;

(6) temperature depth profile.

When the treatment radiation is laser light, the treatment device may further comprise a skin optical coupler 12, configured to optically couple both the treatment laser beam 22, the probe laser beam 82 and the imaging module optical system 67 to the skin. The coupler 12 may comprise at least one optical element having at least three planar sides, the first side facing the treatment beam 22, the second side facing the probe beam 82 and the third side facing the imaging module optical system 67.

One side of the coupler 12 is in direct contact with the outer surface of the skin, so that a coupling gel is preferred. To minimize index mismatch between the optical coupler 12 and the skin, the optical coupler 12 may be made of a material having a refractive index in the range of 1.36 to 1.46.

The skilled person may wish to adapt the angle 112 between the outer layer of the skin axis 11 and the probe axis 71. It may be advantageous to configure and arrange the measurement device 30, 130, 230, 330, 430 so that this angle 112 is in the range of 45 degrees up to and including 90 degrees. By changing this angle 112, the penetration depth of the probe light beam 82 into the skin can be adjusted.

FIGS. 6A to 6D illustrate schematically the relative angles between the probe axis 71, the imaging optical axis 51 and the outer surface of the skin axis 11 for respectively the first 30 and second 130 embodiment, the third embodiment 230, the fourth embodiment 330 and the fifth embodiment 430.

Figure 6A:
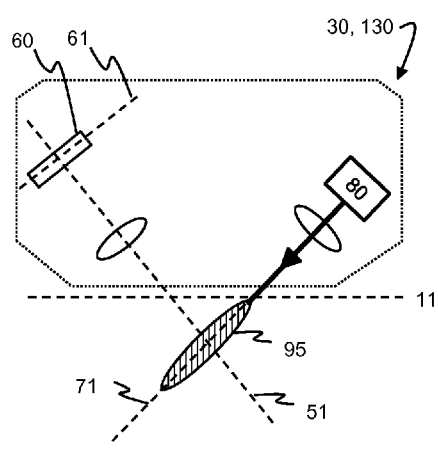

FIG. 6A is included, so that the angles 111, 112 of the different embodiments may be easily compared. The angles depicted are the same as in FIGS. 2 and 4—the angle 111 between the probe axis 71 and the imaging optical axis 51 is about 90 degrees, and the angle 112 between the probe axis 71 and the outer skin layer axis 11 is about 45 degrees.

Figure 6B:
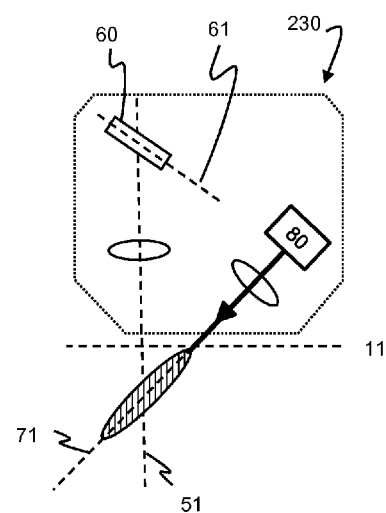

FIG. 6B illustrates the third embodiment 230, in which the angle 111 between the probe axis 71 and the imaging optical axis 51 is about 45 degrees, and the angle 112 between the probe axis 71 and the outer skin layer axis 11 is about 45 degrees. Although the image on the optical detector array 60 may have more aberrations than the configuration of FIG. 6A, the device 230 may be more compact. Additionally, the processor 40 may be configured to correct for the aberrations. As the imaging optical axis 51 is no longer perpendicular to the probe axis 71, one or more lens planes in the imaging optical system 67 will not be parallel to the probe axis 71. To ensure that the detector 60 lies in the image plane, the detector axis 61 will typically need to be arranged at an angle to the imaging optical axis 51 that is equal to the angle 111, which is about 45 degrees in this case. This correction to the detector axis 61 is calculated according to the Scheimpflug principle.

Figure 6C:
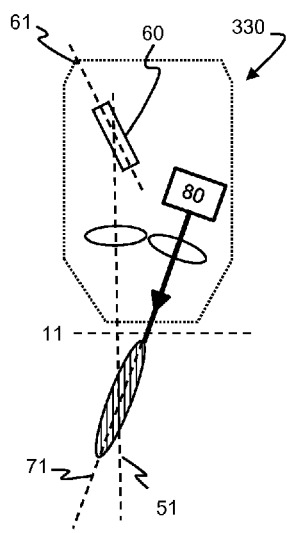

FIG. 6C illustrates a fourth embodiment 330, in which the angle 111 between the probe axis 71 and the imaging optical axis 51 is about 20 degrees, and the angle 112 between the probe axis 71 and the outer skin layer axis 11 is about 45 degrees. Similar to the third embodiment 230, the processor 40 may be configured to correct for additional aberrations, and the detector axis must be corrected, in this case also to an angle of 20 degrees, with respect to the imaging optical axis 51.

Figure 6D:
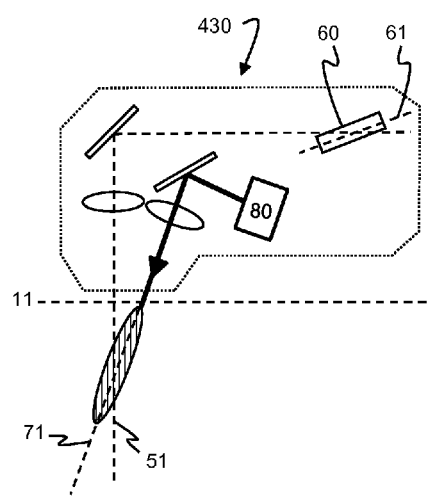

FIG. 6D illustrates a fifth embodiment 430 in which the angles are identical to those indicated in the fourth embodiment 330, but additional mirrors are used to reduce the height of the device 430, defined as the dimension in the direction perpendicular to the outer skin axis, and to increase the length of the device 430, defined as the dimension in the direction of the outer skin axis 11.

In summary, the invention provides a non-invasive measurement device 30 and a method for the measurement of skin properties using laser light, the device comprising a probe module 70 and an imaging module 50. The invention also provides a non-invasive treatment device 130, 230, 330, 430 and a method comprising the measurement device/method. The probe module 70 provides a probe light beam 82 that enters the skin along the probe axis 71. The probe light beam 82 is separate from any treatment radiation beam 22, so that the probe light beam 82 can be optimized for the measurement. A more reliable skin measurement system is provided because it measures a plurality of positions along the probe axis 71, within a probe region 95. As the treatment location 90 is or will be comprised within this probe region 95, the invention measures the skin properties at the treatment location 90 and the surrounding points along the probe axis 71. The imaging module 50 is configured and arranged such that the plurality of points are imaged on an optical detector array 60, so that all the points are measured at the same time. In other words, the measurement device 30, 130, 230, 330, 430 measures the optical depth profile of the section of probe axis 71 comprising the plurality of points. The skin parameters measured may then be used to set or modify the treatment parameters, or to indicate that no further treatment is required.

The measurement device and method may also comprise a treatment module 110 or treatment step. The skin parameters measured may then be directly used to control the treatment parameters. This provides a skin treatment device 10 that is both effective and delivers reproducible results.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer.

The word "module" should not be interpreted to mean that the functionality and hardware are distinguishable in the device. It is used to indicate a functionality which the device comprises, and in practice different "modules" may use in part or entirely the same hardware and optical components.

In the device claim enumerating several means, several of these means may be embodied by one and the same item of hardware. The mere fact that certain measures are recited in mutually different dependent claims does not indicate that a combination of these measures cannot be used to advantage.

OVERVIEW OF REFERENCE NUMBERS 10 (Skin) treatment device
110 (Skin) treatment module
11 Outer surface of skin axis
12 Radiation coupler, for example optical coupler
16 Epidermis layer of skin
17 Dermis layer of skin
20 Treatment radiation source, for example laser light or radio-frequency source
21 Treatment axis
22 Treatment radiation beam, for example laser light or radio-frequency beam
27 Treatment beam-shaping and directing components, for example waveguides or optical components
30 Skin measurement device, first embodiment
40 Processing unit
50 Imaging module
51 Imaging optical axis
60 Optical detector array
61 Detector axis
63 Detector mask
65 Light detection elements
67 Imaging optical system, second optical system
70 Probe module
71 Probe axis
80 Probe laser light source
82 Probe laser beam
87 Probe optical system, first optical system
90 Treatment location, for example focus of laser light
95 Probe region
111 Angle between imaging optical axis (51) and probe axis (71)
112 Angle between probe axis (71) and the outer surface of the skin
130 Skin treatment device, second embodiment (comprising treatment, probe and imaging)
131 Directing optical element
132 Beam splitting optical element
137 Treatment and probe optical system, third optical system
160 Optical detector array, second embodiment
230 Skin treatment device, third embodiment (comprising treatment, probe and imaging)
260 Optical detector array, third embodiment
330 Skin treatment device, fourth embodiment (comprising treatment, probe and imaging)
430 Skin treatment device, fifth embodiment (comprising treatment, probe and imaging)

The invention claimed is:

1. A non-invasive measurement device for measurement of skin properties using laser light, the device comprising:
   a probe module comprising:
      a laser light source configured to generate a probe light beam along a probe axis and impinge on an outer surface of a skin to be treated; and
      a first optical system configured to direct the probe light beam to a probe region inside the skin; and
   an imaging module, comprising:
      a second optical system comprising:
         an imaging optical axis that intersects with the probe axis; and
         an optical detector array, disposed along a detector axis in an image plane, comprising a plurality of light detection elements arranged in a plurality of rows and a plurality of columns, wherein the plurality of columns are positioned along the detector axis;
      the second optical system configured to:
         combine outputs of the plurality of light detection elements within one of: a same row and a same column received at a same time, wherein the outputs of the plurality of light detection elements are combined separately from the outputs of the plurality of light detection elements in another one of said plurality of rows or said plurality of columns, the outputs corresponding to a plurality of probe positions distributed along the probe axis within the probe region;

form an image based on the combined outputs; and generating at least one control parameter associated with at least one of: the probe module and the imaging module based on the formed image, wherein said at least one control parameter altering at least one of: the laser light and the forming of said image.

2. A measurement device according to claim 1, wherein the detector axis is comprised in a plane that comprises the probe axis and the imaging optical axis.

3. The measurement device according to claim 1, wherein an angle enclosed by the probe axis and the imaging optical axis is in a range of 20 to 90 degrees.

4. The measurement device according to claim 1, wherein an angle enclosed by the probe axis and the skin outer surface is in a range of 45 to 90 degrees.

5. The measurement device according to claim 1, wherein an angle enclosed by the detector axis and the imaging optical axis is corrected according to a Scheimpflug principle.

6. The measurement device according to claim 1, wherein the optical detector array comprises:

a matrix of Y light detection elements extending along the detector axis and X light detection elements extending along an axis perpendicular to the detector axis, wherein a ratio of said Y light detector elements to said X light detector elements is greater than 5 to 1.

7. A non-invasive treatment device for treatment of skin using electromagnetic treatment radiation, the device comprising:

a probe module comprising:

a laser light source configured to generate a probe light beam along a probe axis and impinge on an outer surface of a skin to be treated; and a first optical system configured to direct the probe light beam to a probe region inside the skin; and an imaging module, comprising:

a second optical system comprising:

an imaging optical axis that intersects with the probe axis; and an optical detector array, disposed along a detector axis in an image plane, comprising a plurality of light detection elements arranged in a plurality of rows and a plurality of columns, wherein the columns are positioned along the detector axis;

the second optical system configured to:

combine, outputs of the plurality of light detection elements received at a same time within one of: a same row and a same column, wherein the outputs of the plurality of light detection elements are combined separately from the outputs of the plurality of light detection elements in another one of said plurality of rows and said plurality of columns, the outputs of the plurality of light detection elements corresponding to a plurality of probe positions distributed along the probe axis within the probe region; and form an image based on the combined outputs of the plurality of light detection elements, wherein at least one control parameter is generated based on the formed image; and a treatment module comprising:

a treatment radiation source configured to:

provide a treatment radiation beam along a treatment axis that impinges on the outer surface of the skin to be treated; and beam-shaping and directing components; configured to direct the radiation treatment beam to a treatment location disposed within the probe region, wherein the at least one control parameter is associated with at least one of: the probe module, the imaging module and the treatment radiation source, wherein the at least one control parameter altering at least one parameter associated with at least one of: the probe module, the imaging module and the treatment module.

8. The treatment device according to claim 7, wherein the treatment radiation source is laser light, and the treatment axis coincides with the probe axis.

9. A method for non-invasive measurement of skin properties using a device generating laser light, the device comprising a probe module and an imaging module, the method comprising:

transmitting a probe light beam along a probe axis, said probe light beam impinging on an outer surface of a skin to be treated;

directing the probe light beam to a probe region inside the skin;

detecting, by an optical detector array disposed along a detector axis in an image plane wherein the optical detector array having an imaging optical axis that intersects with the probe axis;

combining outputs of a plurality of light detection elements received at a same time, wherein the outputs of the plurality of light detection elements in one of: a same row and a same column are combined separately from the outputs of the plurality of light detection in another row or another column;

forming an image based on the combined outputs of the plurality of light detection elements;

processing the image to generate one or more control parameters;

applying the one or more control parameters to alter at least one parameter associated with at least one of: transmitting a probe light beam and forming said image.

10. A measurement method according to claim 9, wherein the detector axis is comprised in a plane which comprises the probe axis and the imaging optical axis.

* * * * *